US009401625B2

(12) United States Patent
Zottola et al.

(10) Patent No.: US 9,401,625 B2
(45) Date of Patent: Jul. 26, 2016

(54) SOLAR-POWERED EXTERNAL CHARGER AND SOLAR-POWERED EXTERNAL CHARGER CRADLE FOR MEDICAL IMPLANTABLE DEVICE SYSTEMS

(71) Applicant: Boston Scientific Neuromodulation Corporation, Valencia, CA (US)

(72) Inventors: Dennis Zottola, Ventura, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 220 days.

(21) Appl. No.: 14/271,166

(22) Filed: May 6, 2014

(65) Prior Publication Data
US 2014/0354211 A1  Dec. 4, 2014

Related U.S. Application Data

(60) Provisional application No. 61/830,503, filed on Jun. 3, 2013.

(51) Int. Cl.
*H01M 10/46* (2006.01)
*H02J 7/35* (2006.01)
*A61N 1/378* (2006.01)
*H02J 7/00* (2006.01)
*H02J 7/02* (2016.01)

(52) U.S. Cl.
CPC .............. *H02J 7/35* (2013.01); *A61N 1/3787* (2013.01); *H02J 7/0044* (2013.01); *H02J 7/0054* (2013.01); *H02J 7/0055* (2013.01); *H02J 7/025* (2013.01); *H02J 7/355* (2013.01)

(58) Field of Classification Search
CPC ......... H02J 5/005; H02J 7/025; H02J 7/0042; H02J 7/355; A61N 1/32; A61N 1/05
USPC .......... 320/107, 108, 114, 15; 607/33, 61, 65, 607/103, 150
See application file for complete search history.

(56) References Cited

U.S. PATENT DOCUMENTS

| 7,003,353 | B1 | 2/2006 | Parkhouse |
| 7,570,994 | B2 * | 8/2009 | Tamura ................ A61N 1/3975 320/111 |
| 7,957,804 | B2 | 6/2011 | Abreu |
| 7,979,126 | B2 | 7/2011 | Payne et al. |
| 8,214,042 | B2 | 7/2012 | Ozawa et al. |
| 2003/0176892 | A1 * | 9/2003 | Shalev .............. A61M 5/14276 607/3 |
| 2007/0208403 | A1 * | 9/2007 | Della Santina .... A61N 1/36032 607/137 |

(Continued)

OTHER PUBLICATIONS

Boston Scientific, "Precision Spinal Cord Stimulator System Clinician Manual," at 38-39 (Apr. 2011).
LTC1733 Data Sheet, Linear Technology Corp. (date unknown).

(Continued)

*Primary Examiner* — Edward Tso
(74) *Attorney, Agent, or Firm* — Lewis, Reese & Nesmith, PLLC

(57) ABSTRACT

Disclosed are an external charger including a solar cell array for charging or powering an implantable medical device (IMD), and a cradle including a solar cell array for charging or powering an external charger for charging or powering an implantable medical device. The disclosed improved external charger or improved cradle are particularly beneficial for charging a battery in an external charger used to charge or power an IMD when a power source is otherwise unavailable, such as a wall socket.

26 Claims, 9 Drawing Sheets

(56) References Cited

U.S. PATENT DOCUMENTS

2008/0027500 A1    1/2008    Chen
2008/0300660 A1*   12/2008   John .................... A61N 1/3785
                                                                    607/61

OTHER PUBLICATIONS

NCP802 Data Sheet, ON Semiconductor / Semiconductor Components Indus., LLC (2004).
SLMD121H10 Data Sheet, IXYS Corp (2010).

* cited by examiner

SOLAR-POWERED EXTERNAL CHARGER AND SOLAR-POWERED EXTERNAL CHARGER CRADLE FOR MEDICAL IMPLANTABLE DEVICE SYSTEMS

CROSS-REFERENCE TO RELATED APPLICATIONS

This is a non-provisional application of U.S. Provisional Patent Application Ser. No. 61/830,503, filed Jun. 3, 2013, which is incorporated by reference in its entirety, and to which priority is claimed.

FIELD OF THE INVENTION

The present invention relates generally to implantable medical device systems, and, more particularly, to solar-powered external devices useable in implantable medical device systems.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

As shown in FIG. 1, a SCS system typically includes an Implantable Pulse Generator (IPG) 100, which includes a biocompatible device case 102 formed of titanium for example. The case 102 typically holds the circuitry and battery 104 necessary for the IPG to function. The IPG 100 is coupled to electrodes 116 via one or more electrode leads (two such leads 114a and 114b are shown), such that the electrodes 116 form an electrode array 110. The electrodes 116 are carried on a flexible body 118, which also houses the individual signal wires 112a-112p coupled to each electrode. The signal wires 112a-112p are connected to the IPG 100 at one or more lead connectors 106 fixed in a header 108, which can comprise an epoxy for example. In the illustrated embodiment, there are eight electrodes on lead 114a, labeled E1-E8, and eight electrodes on lead 114b, labeled E9-E16, although the number of leads and electrodes is application specific and therefore can vary. In a SCS application, electrode leads 114a and 114b are typically implanted on the right and left side of the dura within the patient's spinal cord. These proximal end of leads 114a and 114b are then tunneled through the patient's flesh to a distant location, such as the buttocks, where the IPG case 102 is implanted, at which point they are coupled to the lead connector(s) 106.

As shown in the cross section of FIG. 3, IPG 100 typically comprises an electronic substrate assembly 120 including a printed circuit board (PCB) 122, to which various electronic components 124 are mounted, some of which are described later with reference to FIG. 4. The IPG 100 can further include a telemetry antenna or coil (not shown) for communicating with an external device such as a patient or clinician controller (not shown), which telemetry antenna can be positioned in the header 108 or in the case 102. A charging coil 130 within the case 102 receives a magnetic field 150 from an external charger 200 to charge the IPG's battery 104, as explained further below.

To avoid having to surgically replace the IPG 100 when its energy is depleted, the IPG 100's battery 104 is typically rechargeable via an external charger 200 as just mentioned. FIG. 2A shows a plan view of the external charger 200, which includes a housing 204 configured to be hand-holdable and portable (akin in size and shape to a cell phone for example), and which is typically constructed of rigid plastic. An indicator 206, such as one or more light-emitting diode LED(s), can display multiple patterns or colors to indicate the status of the external charger 200, such as whether the external charger is actively producing the magnetic field 150, or to indicate the status of a battery 220 in the external charger 200, described further below. An on/off switch 208 activates the external charger 200 to produce the magnetic field 150.

As best shown in the cross section of FIG. 3, the external charger 200 is powered by a battery 220, which can be recharged as described further below. The external charger 200 can contain one or more printed circuit boards 210 and 212 that contains the circuitry 214 needed to implement its functionality, which circuitry is described further with respect to FIG. 4. The hand-holdable external charger housing 204 can include a top surface 204a and a bottom surface 204b, which if formed in separate portions may be snapped together or connected by other means. Note that the top and bottoms surfaces 204a and 204b are substantially planar (within 10 degrees), although they can be slightly angled with respect to one another as shown to accommodate the thickness of the battery 220 if necessary.

The external charger 200 includes a primary charging coil 230, which when provided with an AC current (e.g., when on/off switch 208 is pressed), produces the magnetic field 150 to charge the IPG's battery 104 via inductive coupling. The magnetic field 150 induces an AC current in the IPG's charging coil 130, which current is then rectified and used to recharge battery 104 in the IPG 100. Battery 104 in the IPG 100 may comprise a rechargeable polymer lithium-ion battery for example. As one skilled in the art understands, the efficiency of energy transfer between the coils 230 and 130, i.e., their coupling, is improved if the planes of the coils are parallel; if the axes around which they are wound are collinear; and if the coils are as close as possible. This means of inductively transferring energy from the external charger 200 to the IPG 100 can occur transcutaneously, i.e., through the patient's tissue 160.

As noted, the external charger 200 is powered by a battery 220, such as a rechargeable lithium-ion battery, which may from time to time become depleted. To recharge the external charger's battery 220, the external charger 200 can be placed in a charging cradle 250, as shown in FIG. 2B. The cradle 250 may have a plastic housing 252 with an indentation or recess 254 generally shaped to hold the external charger housing 204. Cradle contacts 256 within the recess 254 are designed to meet with external charger contacts 202 which pass through the bottom surface 204b of the external charger housing 204 (see FIG. 3), such that when the external charger 200 is resting in the cradle 250, the contacts 202 and 256 touch, and which allows power to transfer from the cradle 250 to the external charger 200, as described further below. The cradle housing 252 can contain cutouts 258 to assist a user in placing and removing the external charger 200 from the cradle 250. LED indicator 206 on the external charger 200 can be used to indicate when charging of the external charger's battery 220 is occurring, or when charging of battery 220 is complete. The cradle may also contain one or more LEDs to indicate the status of charging the battery 220, although this is not shown. The cradle 250 itself, as is typical, can be plugged into a wall socket via power cord 260.

In lieu of a cradle 250, one skilled will realize that battery 220 in the external charger 200 can be recharged by other means. For example, circuitry in the cradle 250 can be formed in a power cord terminating in a coaxial plug (akin to contacts 256), which plug can then be inserted into a coaxial port (akin to contacts 202) on the external charger 200.

FIG. 4 shows the circuitry within the cradle 250, the external charger 200, and the IPG 100. The operation of such circuitry is generally well known, and thus only briefly described.

AC power from a wall socket 401 is transmitted from the power cord 260 to a transformer 262 in the cradle 250. The transformed power is rectified 264 to a DC voltage (e.g., Vdc=5V) and presented to the cradle contacts 256. Capacitor 266 assists in smoothing or filtering the produced DC voltage. (One skilled will recognize that the transformer 262 and rectifier 264 can also be positioned in line with the power cord 260, and hence outside of the cradle 250).

When the external charger 200 is placed in the cradle 250, Vdc is presented to external charger contacts 202, where it is met by circuitry in the external charger 200 for charging its battery 220. Such circuitry includes a charging circuit 234, battery protection circuitry 236, and a MOSFET switch 237. A small noise-decoupling capacitor 232, e.g., 0.1 µF, can be placed between the external charger contacts 202 at the input of the charging circuit 234. Charging circuit 234 provides a charging current, Ibat1, to charge the battery 220, which circuit 234 may comprise Part No. LTC1733, manufactured by Linear Technology Corp. Charging circuit 234 may charge the battery 220 in different charging modes, such as: a trickle charging mode which produces a small Ibat1 until the battery voltage, Vbat1, reaches a first threshold; a normal charging mode which charges the battery with a higher constant current Ibat1 thereafter; and a constant voltage charging mode when Vbat1 reaches a second higher threshold, which charges the battery 220 still further until Ibat drops to an insignificant value. To prevent overcharging or unwanted discharging of the battery 220, battery protection circuitry 236, upon sensing such a condition, can disconnect the battery 220 from its ground 239 by opening switch 237. (Ground 239 may different from the system ground used by other components in the external charger 200). Battery protection circuitry 236 may comprise Part No. NCP802, manufactured by ON Semiconductor, for example.

The external charger 200 also comprises circuitry to produce the magnetic field 150 used to charge the IPG's battery 104, including: a regulator 238, such as a low drop-out voltage regulator, for supplying a clean and predictable power supply voltage, Vdd, for the external charger's electronics; control circuitry 240, which may comprise a microcontroller for example; an amplifier 242 for driving an AC current Ic though the charging coil 230; and a tuning capacitor 244 used to set the frequency of the magnetic charging field 150 produced, which may be 80 kHz in one example. The IPG 100's components are well known, and have been previously described: charging coil 130 receives the magnetic field 150; its induced current is rectified 132 to a DC voltage; which is used to charge the IPG's battery 104, perhaps via charging/protection circuitry 134 as shown.

DETAILED DESCRIPTION

Figure 1:
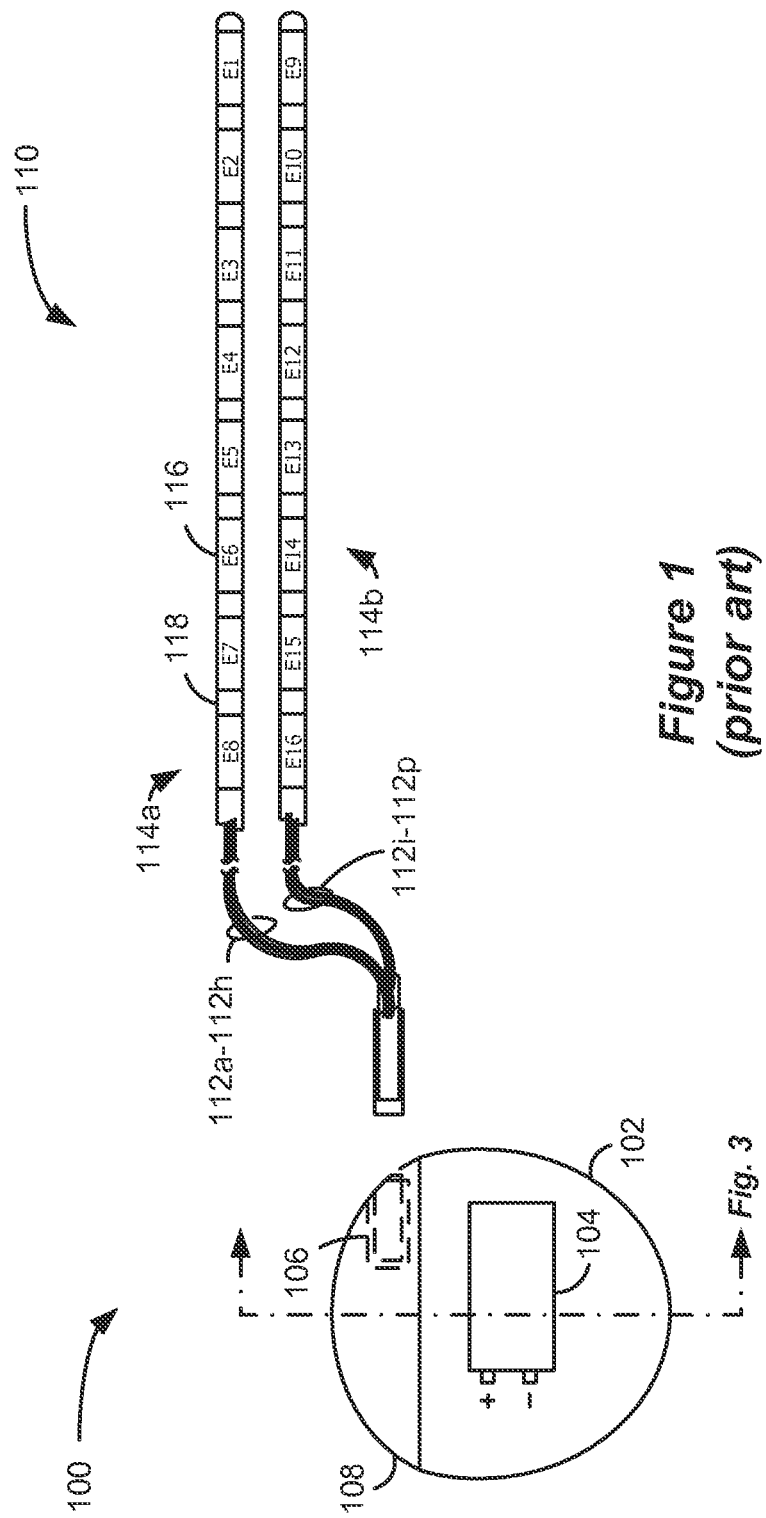
FIG. 1 shows an implantable medical device (IMD) in accordance with the prior art.

A patient having an implanted IPG 100 may need to recharge the IPG's battery 104 using the external charger 200 for anywhere from a few minutes to several hours a day. How much time required for charging will depend on many variables, such as the power consumed by the IPG, the depth at which the IPG is implanted, etc., which vary from patient to patient. When the external charger 200 is not being used to charge the IPG's battery 104, it is normally placed in the cradle 250 to charge its battery 220 in preparation for its next use to recharge the IPG 100.

This works fine when a power source, such as AC power from a wall socket 401 (FIG. 4), is readily available to charge the external charger's battery 220 (via the cradle 250). However, such a power source may not be available to a patient from time to time: she may be outdoors; there may be a power outage; she may be in a country for which she doesn't have a suitable AC wall adapter, etc. If such times are extensive, the external charger's battery 220 cannot be charged; eventually the external charger 200 will become unusable; and the IPG's battery 104 thus can't be charged. This runs the risk of leaving the patient without stimulation therapy.

Figure 5:
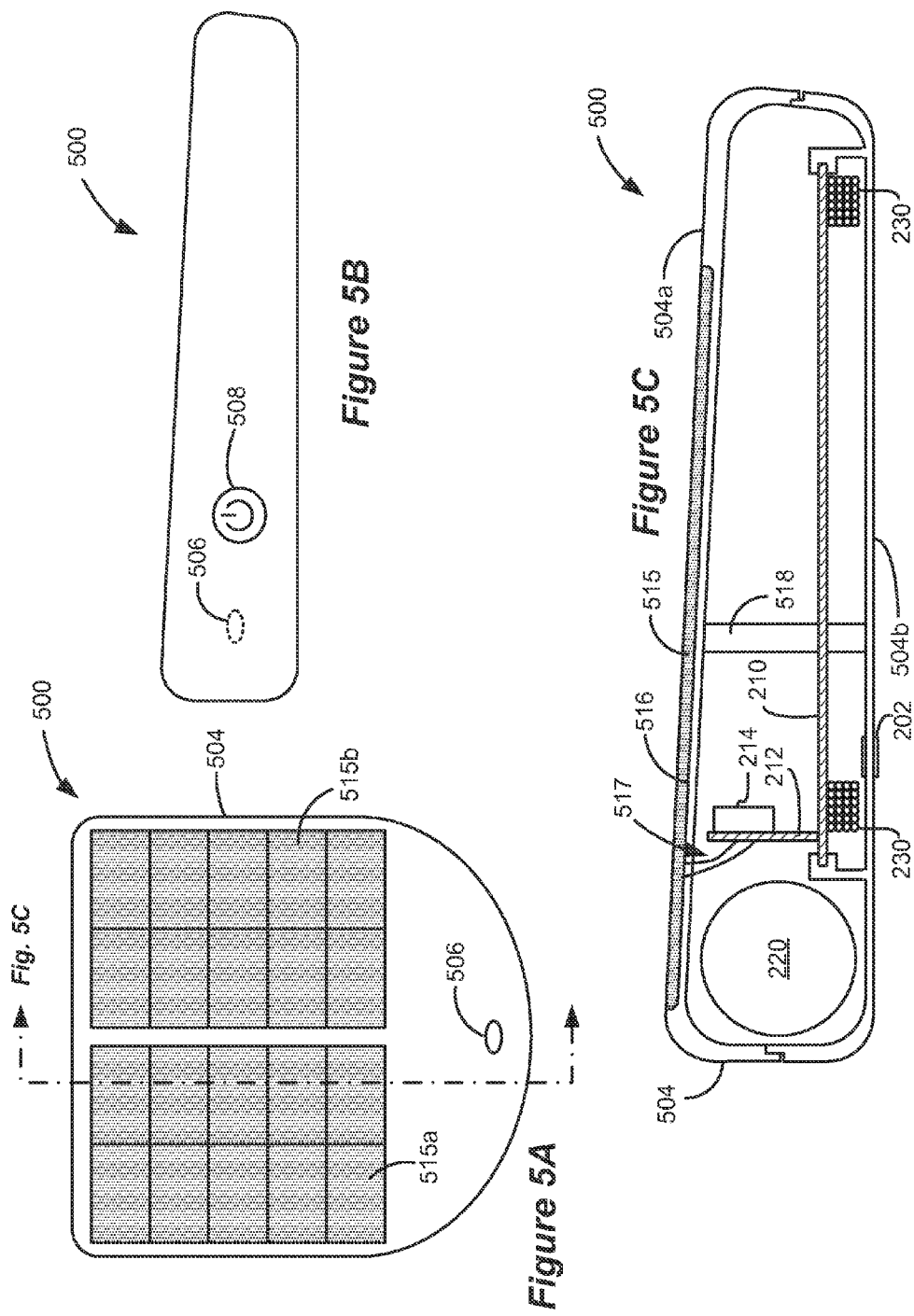
FIGS. 5A-5C show top, side, and cross-sectional views of an improved external charger including a solar cell array in accordance with an embodiment of the invention.

The inventor addresses this problem in a first example by disclosing an external charger 500 that can be charged by solar power. FIGS. 5A-5C show top, side, and cross-sectional views of an embodiment of the external charger 500. The external charger 500 includes a number of improvements over the prior art external charger 200 described in the Background, the chief of these being the addition of a solar cell array 515 and associated circuitry for charging the battery 220 from the solar cells. Solar cell array 515 is used to charge the external charger 500's battery 220 even in environments where a power source (e.g., wall socket 401) is not available, because the battery 220 can be charged by illumination using solar cell array 515 alone. However, as discussed further below, the external charger 500 can also be charged using a traditional power source, such as by using a cradle, as occurred in legacy systems.

In the example shown, the solar cell array 515 comprises two solar cells 515a and 515b. The number and shape of the cells in the array 515 can vary, and the number and shapes chosen will depend on a number of factors, such as the available room on the housing 504 of the external charger 500 and the power that the cells produce, etc. If necessary, the housing 504 of the external charger 500 can be modified to better fit the shape and size of commercially-available solar cells. In the example shown, each solar cell 515a and 515b comprise Part No. SLMD121H10, manufactured by IXYS Corp, which are capable of outputting a voltage of up to 5 V.

Each solar cell 515a and 515b may contribute 50 mA of current at 4 V for charging the battery 220 when subject to high illumination in direct sunlight for example. If 1000 mAh of charge is required to fully charge battery 220, then the solar cell array 515 can charge the battery 220 in about 10 hours. Additional solar cells can be used to charge battery 220 more quickly. Likewise, when receiving less than full illumination, such as when the external charger 500 receives only indoor lighting, the time needed to charger battery 220 will be longer.

In the example shown, many of the user interface elements have been moved from the top surface 504a of the external charger 500 to maximize the room available for the solar cell array 515. For example, in FIG. 5B, it is seen that the on/off switch 508 has been moved to the side of the housing 504. The indicator 506 (e.g., LED(s)) is relatively small, and thus may remain on the top surface 504a of the housing as shown in FIG. 5A, although it can optionally be moved to the side as well, as shown in FIG. 5B. Indicator 506, in addition to functioning as did the indicator 206 of the prior art external charger 200, may indicate when the external charger 500's battery 220 is being charged from power produced by the solar cell array 515, such as by changing the color or pattern of illumination of the indicator 506.

Figure 3:
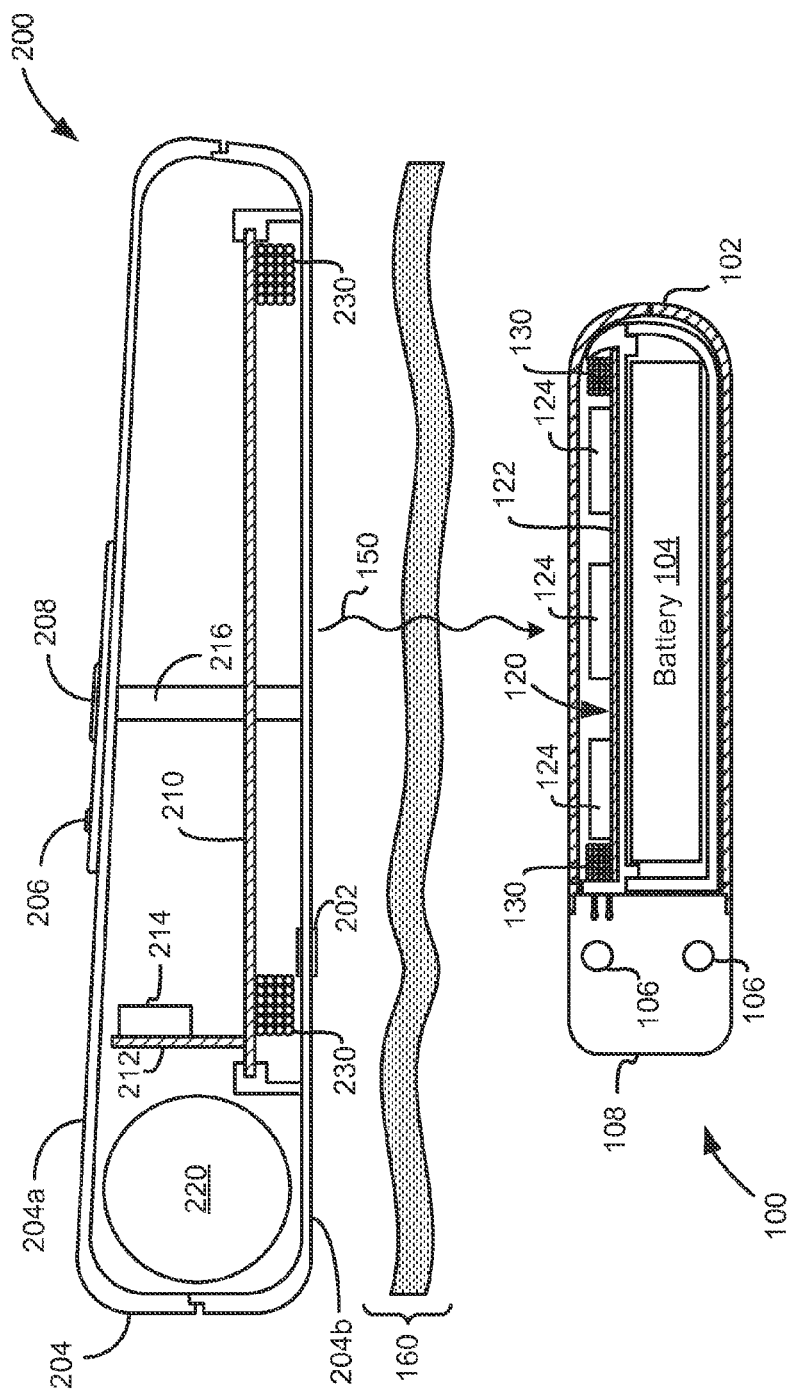
FIG. 3 shows a cross section of the IMD in relation to the external charger in accordance with the prior art.

As best seen in FIG. 5C, the solar cell array 515 may be recessed 516 within the material used to form the top of the external charger 500's housing 504, such that the top of the solar cell array 515 is flush with the top of the housing 504. This is preferred as a means of protecting the solar cells 510 from mechanical damage, as well as allowing the external charger 500 to be easily slipped into various retaining means such as a charging belt, which will be discussed with respect to FIG. 7. However, such recessing of the solar cell array 515 is not strictly necessary, and they may instead be affixed (e.g., glued) to the top surface of the housing 504. A support 518 may be used to prevent the top and bottom of the housing 504 from deforming under pressure, which might otherwise cause the solar cell array 515 to crack. (Compare support 216 in the prior art external charger 200 (FIG. 3), which is similarly used to prevent damage to the on/off switch 208). Lead wires 517 can be used to connect the solar panels to the circuitry, such as one of PCBs 212 or 210.

As best seen in FIG. 5C, the charging coil 230 is proximate to the bottom surface of the housing 504, while the solar cell array 515 is coupled to the top surface of the housing. Spacing the solar cell array 515 and the charging coil 230 in this manner is useful to prevent the solar cell array from interfering with the magnetic field produced by the charging coil. Additionally, this places the solar cell array 515 in a logical position where it would be expected to receive the best illumination (on the top), and places the charging coil 230 is a logical position where coupling to the charging coil 130 in the IPG 130 is maximized (proximate the bottom).

Figure 6:
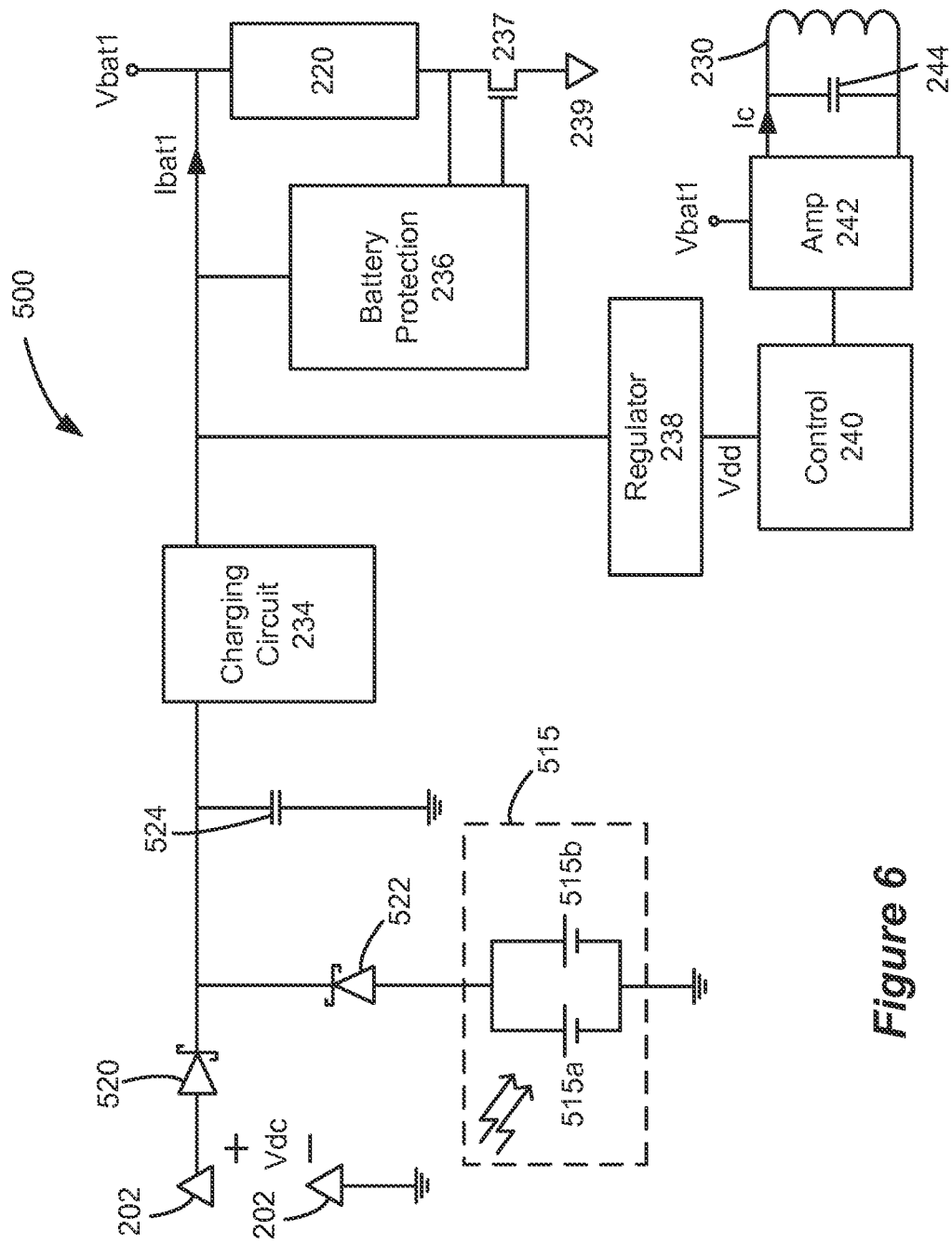
FIG. 6 shows circuitry of the improved external charger in accordance with an embodiment of the invention.

FIG. 6 shows the circuitry within the external charger 500. Many of the circuit elements of external charger 500 do not differ from external charger 200 discussed in the Background, and hence such elements are not again discussed here. New to the circuitry is the solar cell array 515, two diodes 520 and 522, and capacitor 524. In this embodiment, the two solar cells 515a and 515b are connected in parallel to double the current that the array 515 provides. However, the solar cells in the array 515 can also be connected in series. Whether solar cells are connected in parallel or in series, or combinations of these, will depend on the power they are capable of producing, as well as the voltage they output, and how well that voltage matches the desired input voltage of the charging circuit 234.

Diodes 520 and 522 are preferably Schottky diodes that provide a low forward-voltage drop while protecting against reverse current flow. Diode 520 prevents backflow through the charger contacts 202 when the solar cell array 515 is producing current, while diode 522 prevents backflow through the solar cell array 515 when Vdc as supplied from the cradle 250 is presented to the charger contacts 202. Diode 520 is not strictly needed, as diodes typically present in the rectifier 264 in the cradle 250 (FIG. 4) should prevent current generated by the solar cell array 515 from flowing back through the charger contacts 202. The cathodes of diodes 520 and 522 are tied together at the input to charging circuit 234 such that current provided from either the charger contacts 202 (as supplied by cradle 250) or the solar cell array 510 may be used to power the charging circuit 234. Charging of the battery 220 can thus occur using either Vdc (though diode 520) or the solar cell array 510 (through diode 522) without the need for switching or selection of either of these means. In other words, the voltage provided by both of these means is not provided to the input of the charging circuit 234 through a switch. This simplifies design, as control circuitry 240 for example is not burdened with selecting either as the input to the charging circuit 234.

Capacitor 524 is also connected to the input node of the charging circuit 234. Capacitor 524 is preferably much larger than capacitor 232 (FIG. 4) of the external charger 200 discussed in the Background, which helps to regulate the "duty cycle" with which the charging circuit 234 operates. The charging circuit 234 requires a minimum input power to operate. The solar cell array 510 may not be able to provide such minimum input power continuously (particularly in low illumination). This will means that the charging circuit 234 will operate intermittently to charge the external charger's battery 220—providing Ibat1 when the solar cell array 515 has generated a significant charge, and then ceasing to operate once that charge is depleted. Storing charge capacity on the relatively-large capacitor 524 regulates the time constant of the voltage presented to the input of the charging circuitry 234, and thus stabilizes and extends the time periods that the charging circuit 234 is either on or off to generate Ibat1 to charge the battery 220.

The external charger 500 retains charger contacts 202, and thus the battery 220 in the external charger 500 can still be charged using a charging cradle as occurred in legacy systems, and as described earlier. If the external charger 500 is placed in a cradle, the cradle will produce Vdc=5V at its charger contacts (e.g., 256, FIG. 2B) as before. This voltage may reverse bias diode 522 and thus prevent the solar cell array 515 from providing power to the input of the charging circuit. In other words, if the external charger is physically coupled to a source of power to charge its battery 220 (such as by the cradle 250) such that Vdc is present at the upper node of contacts 202, that means of charging may take precedence and may automatically prevent the solar cell array 515 from reaching the input of the charging circuit 234 without active controlling or switching to choose a particular input for the charging circuit 234, as discussed earlier. However, this is not strictly necessary, and solar cell array 515 may also contribute power to the input of the charging circuit 234 even if Vdc is present.

Figure 7:
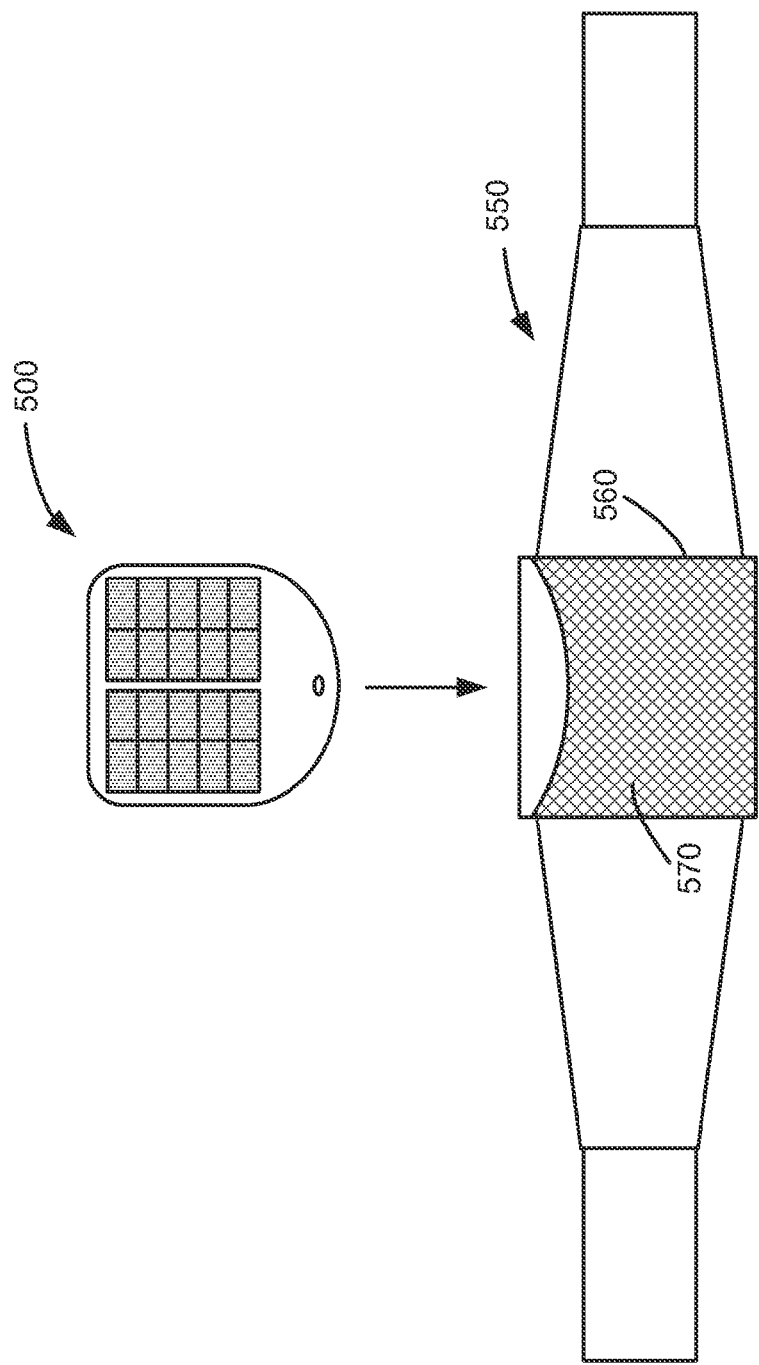
FIG. 7 shows a belt for holding the improved external charger in accordance with an embodiment of the invention.

FIG. 7 shows a belt 550 for holding external charger 550 in a pouch 560. Such belts are typical to position an external charger relative to the implant it charges during a charging session. For example, in an SCS application in which an IPG 100 is positioned in an upward location in a patient's buttocks, a belt is configured to be positioned around a patient waist, with the pouch 560 positionable behind the patient to bring the external charger and IPG into close proximity and to facilitate IPG battery charging. Pouch 560 in FIG. 7 is formed of a translucent material, such as a mesh or clear plastic, thus allowing the solar panel array 515 to charge the external charger's battery 220 while it sits within. If necessary, the pouch 560 may contain holes or ports (not shown) to allow a user access to the on/off switch 508 (FIG. 5B) for example.

Figures 2A, 2B:
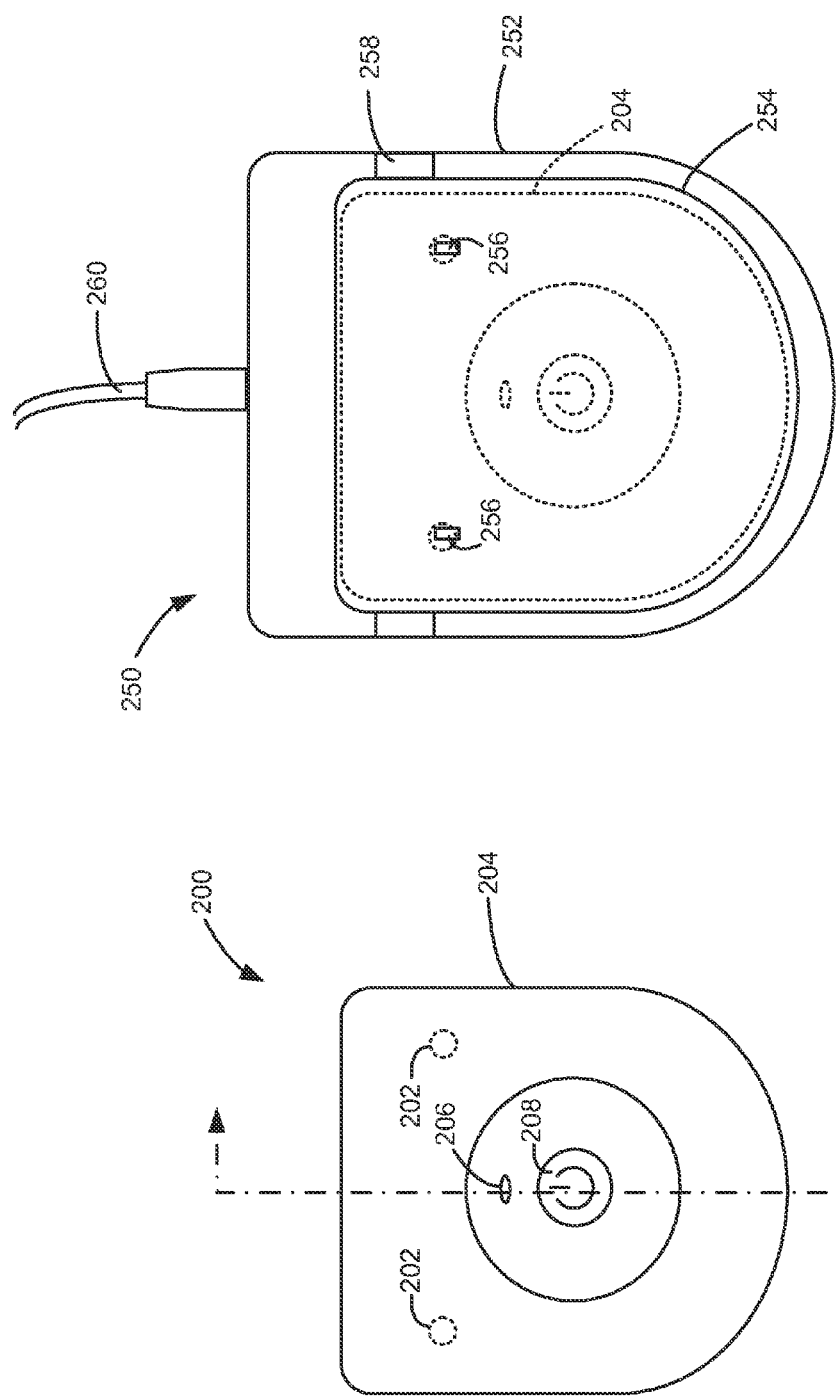
FIG. 2A shows an external charger for charging the IMD in accordance with the prior art.
FIG. 2B shows a cradle for charging the external charger in accordance with the prior art.
Figure 4:
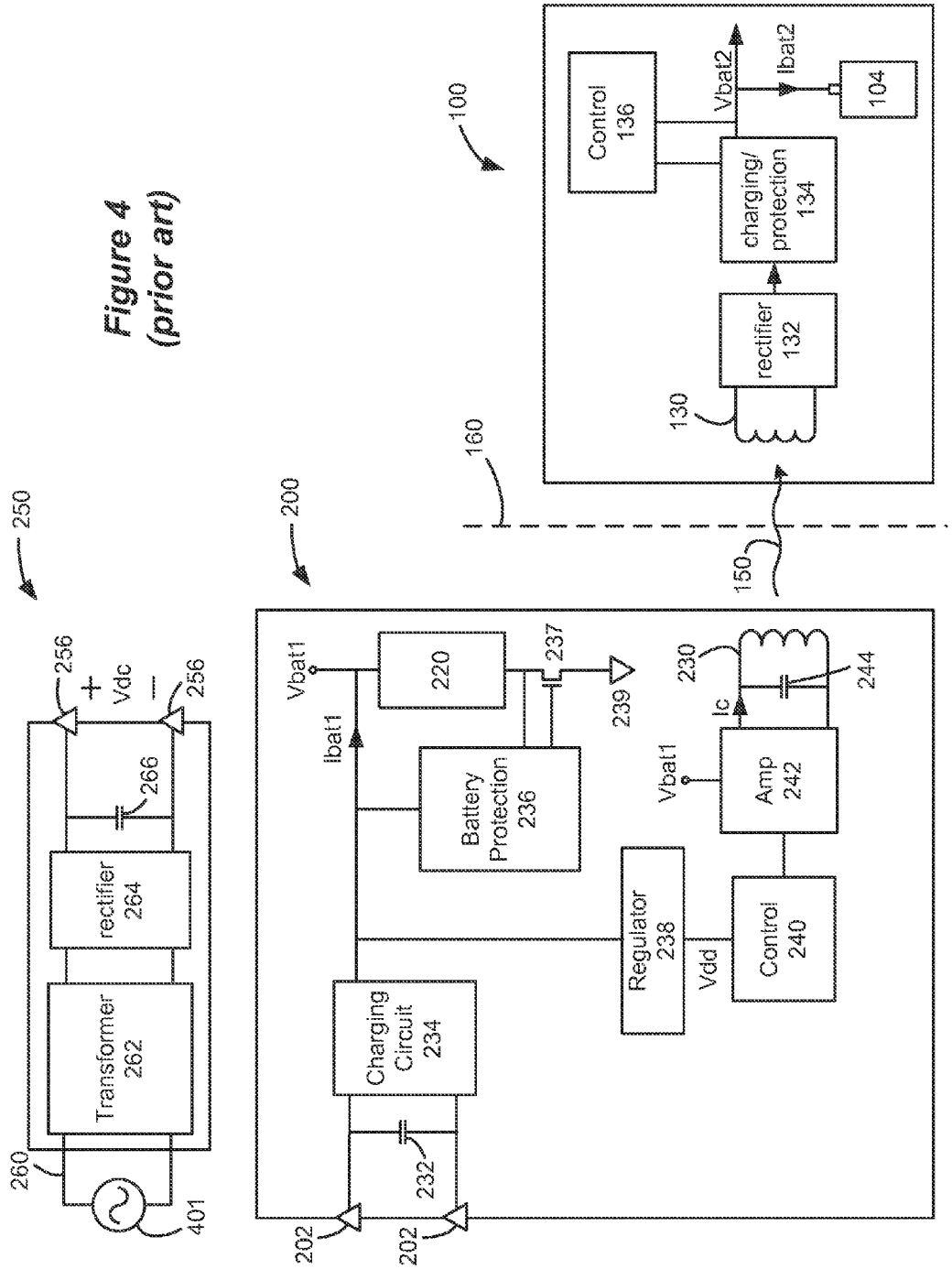
FIG. 4 shows relevant circuitry of the IMD, external charger, and cradle in accordance with the prior art.
Figure 8:
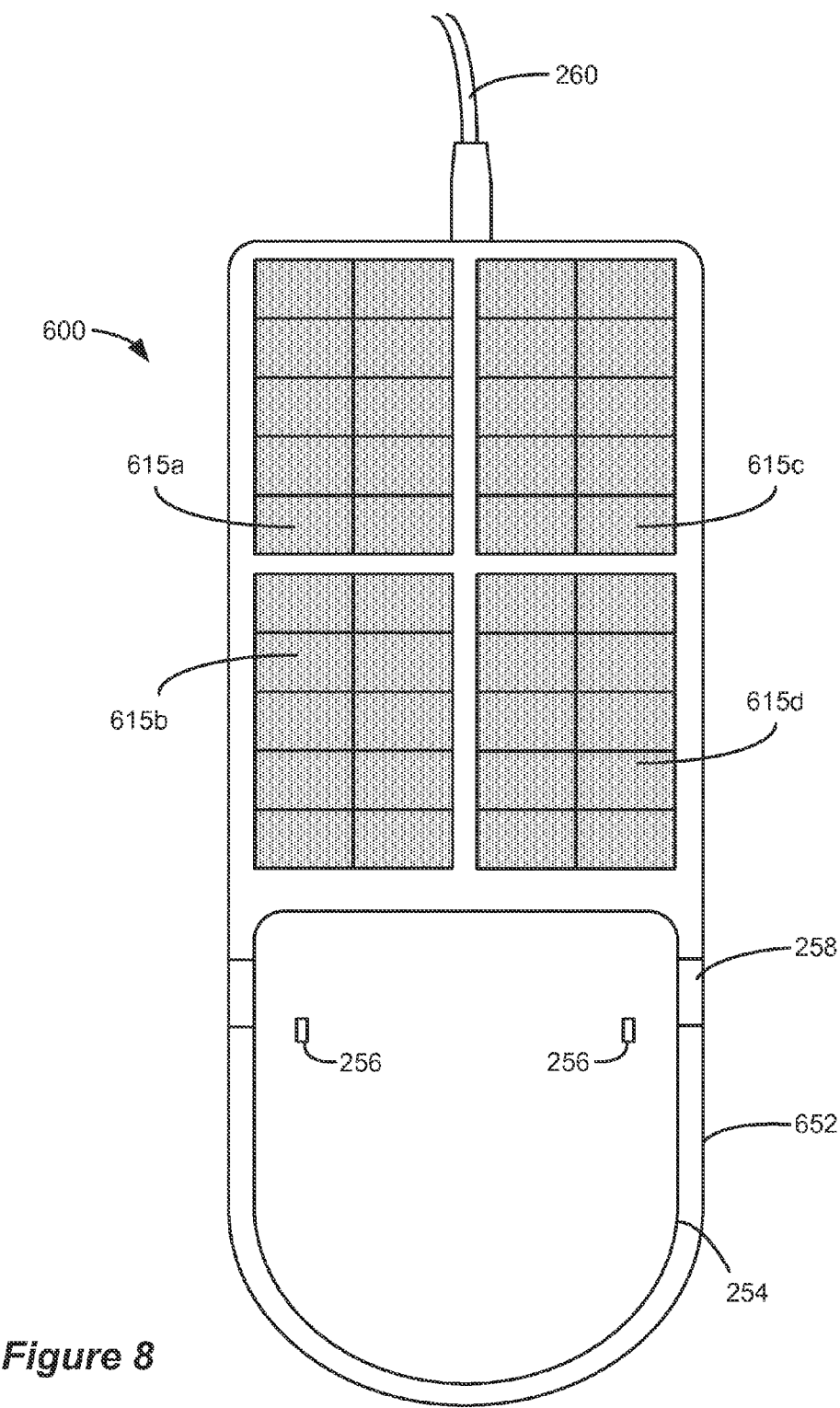
FIG. 8 shows an improved cradle with a solar cell array for charging an external charger in accordance with an embodiment of the invention.

Solar charging can also be used to provide power to an improved cradle 600, as shown in FIG. 8. A solar-powered cradle 600 is useful for the same reasons mention earlier, particularly if a power source (e.g., wall socket 401; FIG. 4) is not available to a patient for an extended period of time. A solar-powered cradle 600 is particularly useful if the external charger itself is not solar-powered (e.g., charger 200; FIG. 2A).

In the example shown, the cradle 600 comprises a solar cell array 615 comprising four solar cells 615a-615d. The cradle 600 has a housing 652 which when compared to the housing 252 of cradle 250 has been elongated to accompany the solar cell array 615. The cradle may generally be made larger than the external charger, and thus may have, or be altered to have, a larger surface area to accommodate more solar cells. Otherwise, the cradle 600 is constructed as described earlier, with an indentation or recess 254 generally shaped to hold the external charger housing, cradle contacts 256 for meeting with the charger contacts 202, a power cord 260, etc. The solar cell array 615 can be recessed in the housing 652 to prevent mechanical damage as described earlier. Cradle 600 can be used to recharge either legacy external charger 200, or the improved solar-powered charger 500 disclosed earlier.

Figure 9:
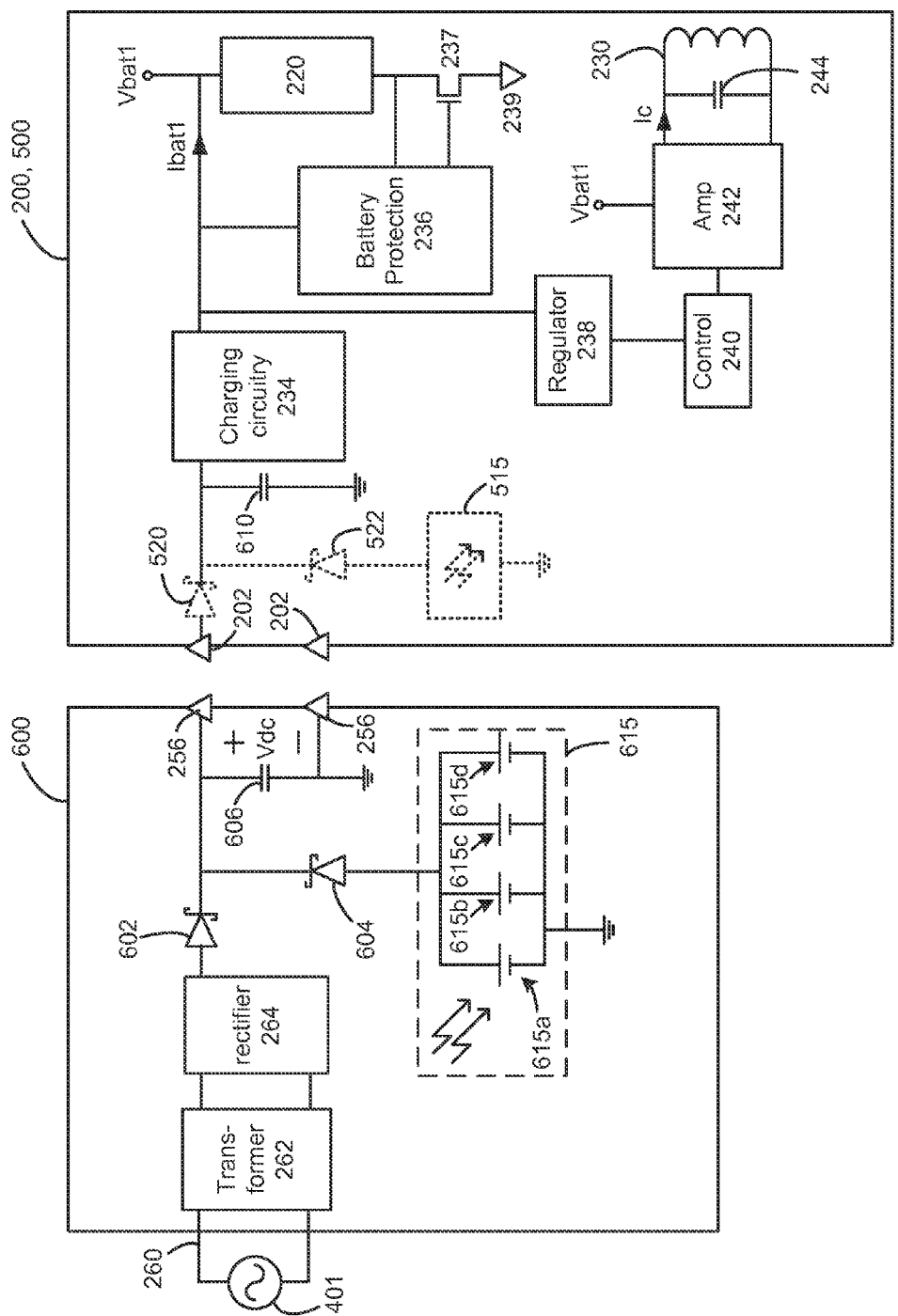
FIG. 9 shows relevant circuitry for the improved cradle in accordance with an embodiment of the invention.

FIG. 9 shows the circuitry within the cradle 600 in relation to a legacy external charger 200 or a solar-powered external charger 500 to be charged. Note that aspects unique to the solar-powered external charger 500 discussed earlier are shown in dotted lines.

The solar cell array 615 in cradle 600 operates somewhat similarly to the solar cell array 515 in the charger 500. As before, two Schottky diodes 602, 604 are present, presenting power from either the rectifier 264 (via the wall socket 401 and transformer 262) or the solar cell array 615 to the cradle contacts 256 used to charge the battery 220 in external charger 200 or 500. In short, Vdc at the cradle contacts can be provided either by legacy means (wall socket 401/transformer 262/rectifier 264) or by the solar cell array 615. Diode 602 is not strictly needed, as diodes (not shown) typically present in the rectifier 264 should prevent current generated by the solar cell array 615 from flowing through the rectifier 264. However, diode 604 prevents backflow through the solar cell array 615 when rectifier 264 is active to supply power to the cradle contacts 256. Diode 604 further acts to provide precedence to rectifier 264 in providing power to the contacts 256, as this diode will be reverse biased when the rectifier 264 is operating to produce Vdc.

If a solar-power external charger 500 is used in conjunction with the solar-powered cradle 600, the power provided by both arrays 615 and 515 can add to present a stronger signal to the input of the charging circuitry 234 used to charge the external charger's battery 220, and hence reduce the time needed to charge that battery. In this case, it may be advisable take measures to ensure that power generated from one array doesn't take precedence over, and thus effectively cancel contribution from, the other array. For example, it may be desirable to remove diode 520 from the external charger 500 to ensure that arrays 615 and 515 see equivalent paths to the input of the charging circuit 234, with each proceeding only through single diodes 604 and 522 respectively.

A "solar cell" as used herein should be understood as including a photovoltaic material or device capable of generating a voltage or current upon exposure to radiation such as light, or arrays comprising more than one of the same.

Although the disclosed improved external charger and external charger cradle are believed most useful in implantable medical device systems having implantable medical devices containing recharger batteries, such as battery 104, the invention is not so limited. Implants without batteries or other internal source of power can be externally powered by the disclosed external charger (which may in turn be charged by the disclosed cradle). In implantable medical device systems that rely on external chargers for a source of continuous power, a solar-powered external charger may be of assistance. Even if such external chargers also contain a battery, the use of solar power can be used to supplement the battery, or supplant it altogether, at least during daytime conditions.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external charger for providing power to an implantable medical device, comprising:
   a housing containing a charging coil configured to produce a magnetic field to provide power to the implantable medical device;
   a battery within the housing configured to provide power to the charging coil for producing the magnetic field;
   a charge circuit within the housing configured to provide a charging current to the battery, wherein the charge circuit is powered at an input;
   a solar cell coupled to the housing and configured to produce a first voltage at the input through a first diode when exposed to illumination; and
   a node configured to provide the input a second voltage when connected to a power source,
   wherein neither the first voltage nor the second voltage are provided to the input through a switch.

2. The external charger of claim 1, wherein the housing is configured to be hand-holdable and portable, or to be worn by a patient.

3. The external charger of claim 1, wherein the node comprises a contact on the housing.

4. The external charger of claim 3, wherein the contact is configured to meet with a cradle contact when positioned in a cradle.

5. The external charger of claim 1, wherein the node provides the second voltage to the input thought a second diode.

6. The external charger of claim 1, wherein the housing comprises a rigid plastic.

7. The external charger of claim 1, wherein the housing comprises a top surface and a bottom surface, wherein the charging coil is proximate to the bottom surface, and wherein the solar cell is coupled to the top surface of the housing.

8. The external charger of claim 7, wherein the solar cell is recessed within the top surface of the housing.

9. The external charger of claim 1, further comprising an amplifier coupled to the charging coil, wherein the battery is configured to power the amplifier to provide the power to the charging coil for producing the magnetic field.

10. The external charger of claim 1, wherein the power source is derived from a wall socket.

11. The external charger of claim 1, wherein the power source comprises a charging cradle configured to hold the housing of the external charger.

12. An external charger for providing power to an implantable medical device, comprising:
- a rigid housing comprising a top surface and a bottom surface;
- a charging coil within the housing proximate to the bottom surface configured to produce a magnetic field to provide power to the implantable medical device;
- a battery within the housing configured to provide power to the charging coil for producing the magnetic field;
- a charge circuit within the housing configured to provide a charging current to the battery, wherein the charge circuit receives power at an input; and
- a solar cell coupled to the top surface of the housing and configured to produce a first voltage at the input when exposed to illumination.

13. The external charger of claim 12, wherein the housing is configured to be hand-holdable and portable, or to be worn by a patient.

14. The external charger of claim 13, further comprising a node configured to provide the input a second voltage when connected to a power source.

15. The external charger of claim 14, wherein the power source is derived from a wall socket.

16. The external charger of claim 14, wherein the second voltage prevents the first voltage from reaching the input.

17. The external charger of claim 14, wherein the node comprises a contact passing through the bottom surface of the housing.

18. The external charger of claim 12, wherein the housing comprises a plastic.

19. The external charger of claim 12, wherein the solar cell is recessed within the top surface of the housing.

20. The external charger of claim 12, further comprising an amplifier coupled to the charging coil, wherein the battery is configured to power the amplifier to provide the power to the charging coil for producing the magnetic field.

21. The external charger of claim 12, wherein the top and bottom surfaces are substantially planar.

22. A system, comprising:
- an external charger configured to wirelessly provide power to an implantable medical device from a battery in the external charger; and
- a cradle configured to hold a housing of the external charger, wherein the cradle is electrically coupleable to the external charger and comprises a solar cell, and wherein the cradle is configured to use energy from the solar cell to charge the battery in the external charger when the external charger is electrically coupled to the cradle.

23. The system of claim 22, wherein the cradle comprises a recess configured to hold the housing of the external charger.

24. The system of claim 22, wherein the cradle and the external charger comprise contacts, and wherein the cradle is electrically coupled to the external charger at the contacts when the external charger housing is held in the cradle.

25. The system of claim 22, wherein the external device cradle is additionally configured to use energy from a wall socket to charge the battery in the external charger when the external charger is electrically coupled to the cradle.

26. The system of claim 22, wherein the external charger further comprises an additional solar cell for providing energy to charge the battery in the external charger.

* * * * *